United States Patent [19]

Steeves et al.

[11] 4,445,988

[45] May 1, 1984

[54] MICROGRAPHIC DETECTION OF PLASTIC DEFORMATION IN NICKEL BASE ALLOYS

[75] Inventors: Arthur F. Steeves, Schenectady; Albert E. Bibb, Clifton Park, both of N.Y.

[73] Assignee: The United States of America as represented by the Department of Energy, Washington, D.C.

[21] Appl. No.: 426,448

[22] Filed: Sep. 29, 1980

[51] Int. Cl.$^3$ .................. C25D 5/38; G01N 27/61
[52] U.S. Cl. .................. 204/129.2; 204/1 T; 204/401; 356/32
[58] Field of Search .................. 204/129.2, 1 T, 401; 356/32

[56] References Cited

PUBLICATIONS

D. A. Trotsenko et al., Patent Associated Literature #I163-7510-H, Detection of Fatigue Cracks, Jul. 1975.
M. F. Berezhnitskaya et al., Patent Associated Literature #S134-7602-I, Method of Determining the Residual Macrostress in Solid & Hollow Cylindrical Rods, Sep. 1975.
Spurling et al., Journal of Nuclear Materials 44, No. 3 (Sep.) 1972, 341-344 North-Holland Publishing Co, Amsterdam.
Smirnova et al., Patent Associated Literature, #I16-3-7602-Y Method of Revealing the Deformation Microvoids and Macrostructure of Nickel-Basic Heat-Resistant Alloys, Nov. 1975.

Primary Examiner—T. Tung
Assistant Examiner—Nathan Thane
Attorney, Agent, or Firm—Michael F. Esposito

[57] ABSTRACT

A method for detecting low levels of plastic deformation in metal articles comprising electrolytically etching a flow free surface of the metal article with nital at a current density of less than about 0.1 amp/cm$^2$ and microscopically examining the etched surface to determine the presence of alternating striations. The presence of striations indicates plastic deformation in the article.

6 Claims, No Drawings

MICROGRAPHIC DETECTION OF PLASTIC DEFORMATION IN NICKEL BASE ALLOYS

The United States Government has rights in this invention pursuant to Contract No. DE-AC-12-76-SN00052 between the Department of Energy and General Electric Corporation.

BACKGROUND OF THE INVENTION

This invention is directed to a method of detecting low levels of plastic deformation in metal alloys. In particular, the invention is directed to a method of detecting low levels of plastic deformation in nickel base alloys and stainless steels.

Permanent deformation will take place in metals or alloys whenever they are stressed beyond their elastic limit. In addition, metals stressed beyond their elastic limit will be imparted with a residual stress which may be detrimental, inconsequential, or beneficial depending upon the eventual use of the metal. In the situation where the residual stress would be detrimental, it is of great importance to determine (1) if the stress is present and (2) if present, the location of the stress. In the case of metal alloys, particularly nickel base alloys, residual stress may significantly increase the rate of attack of the metal subject to stress corrosion cracking conditions.

The detection of low levels of plastic deformation is difficult in large structures even with the aid of special detection devices. For this reason, it is the normal practice in the industry to stress relieve these structures whenever engineering analysis indicates the mere probability of significant plastic deformation. While stress relieving these structures compensates for the detrimental effects of residual stress, it remains a costly and time consuming procedure. Accordingly, the development of a simple and effective method of determining low levels of plastic deformation would be of great benefit because it would limit stress relieving procedures to only those structures which actually have experienced significant plastic deformation. Until the development of the method of the present invention there was no simple or effective microscopic technique for determining low levels of plastic deformation.

SUMMARY OF THE INVENTION

It is the primary object of the present invention to provide a method for detecting plastic deformation in metal alloys.

It is a further object of the present invention to provide a method for detecting plastic deformation in nickel base alloys or stainless steels.

It is another object of the present invention to provide a non-destructive detecting method for testing metal alloys to determine if low levels of plastic deformation are present.

It is a still further object of the present invention to provide a microscopic, non-destructive method of testing metal alloys to determine low levels of plastic deformation.

It is still another object of the present invention to provide a non-destructive method for detecting low levels of plastic deformation in nickel base alloys and stainless steels.

It is a further object of the present invention to provide a non-destructive, microscopic method for detecting low levels of plastic deformation in nickel base alloys and stainless steels.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

To achieve the foregoing and other objects and in accordance with the purpose of the present invention, as embodied and broadly described therein, the method of the present invention may comprise preparing the surface of the metal alloy article for microscopic examination and microscopically examining the prepared surface for the presence of alternating striations in the microstructure of the article, said striations indicating plastic deformation in the article.

In a further aspect of the present invention, in accordance with its purposes and objects, the methods of the present invention comprises polishing the surface of the metal alloy article to obtain a substantially flow free surface, etching the surface of the article under conditions which enable subsequent detection of alternating striations which appear in the microstructure of the article, and microscopically examining the etched surface for the presence of alternating striations. The presence of striations indicates that the article has been subjected to plastic deformation. Accordingly, only the articles exhibiting striations within their microstructure are subjected to stress relieving procedures.

In a preferred embodiment of the present invention the metal alloy article is selected from the group consisting of nickel base alloys and stainless steels.

In a further preferred embodiment of the present invention the etching procedure includes electrolytic etching the polished surface with nital at a current density of less than 0.1 amp/cm$^2$. Most preferably, a 5% nital solution is used and the current density is about 0.05 amp/cm$^2$.

In a still further preferred embodiment of the present invention, the etching procedure further includes a second electrolytic etch with about 10% phosphoric acid at a current density greater than 0.1 amp/cm$^2$. Preferably, 0.2 amp/cm$^2$ is utilized.

In another preferred embodiment of the present invention the microscopic examination comprises interference contrast illumination to determine if alternating striations are present in the microstructure of the metal alloy articles.

The significance of the process of the present invention is that it provides a simple, fast and economical procedure to detect plastic deformation in metal alloy articles. By the use of the procedure of the present invention it is possible to determine whenever excessive stress has been applied to an article. The technique of the present invention may be utilized for (1) design check to evaluate stresses in prototypes, (2) a means for evaluating welds and weld designs, (3) quality control and (4) in situ evaluation of shock or accidental overstress. It has been estimated that the microscopic evaluation of the present invention could be finished in 1 to 2 minutes once the article has been polished and etched (1-2 hours). Accordingly, this procedure is extremely fast in comparison with transmission electron microscopy techniques which encompass several days.

Reference will now be made in detail to the present preferred embodiment of the invention.

DETAILED DESCRIPTION OF THE INVENTION

The method of the present invention comprises preparing a metal alloy substrate for microscopic examination for plastic deformation and microscopically examining the prepared surface for the presence of alternating striations in the microstructure of the prepared article. The existence of alternating striations is conclusive evidence that the article has been stressed beyond its elastic limit and permanent deformation has taken place. Preferably, the metal alloy articles are selected from the group consisting of nickel base alloys and stainless steels.

The metal alloy article is prepared for microscopic examination by surface polishing the article to obtain a substantially flow free surface. Preferably, this polishing procedure may be accomplished by conventional metallographic techniques or by chemical attack polishing with a specific etchant. For example, see U.S. Pat. No. 4,305,779 herein incorporated by reference.

The polished metal alloy article is further prepared for microscopic examination by electrolytically etching the article under conditions which enable subsequent detection of alternating striations in the microstructure of the article. Electrolytic etching includes etching with a 5% solution of nital (i.e., 95% methyl or ethyl alcohol and 5% concentrated nitric acid) at a current density of less than about 0.1 amp/cm$^2$. This single electrolytic etching procedure is normally sufficient to enable detection of plastic deformation during surface microscopic examination. However, to attain the optimum results the prepared article may be further etched at a higher current density in phosphoric acid (i.e., 8 parts orthophosphoric acid: 1 part water). Preferably, the second etch is at a current density of about 0.2 amp/cm$^2$.

The prepared surface is then examined microscopically using interference contrast illumination. Oblique or dark field illumination may also be used, but with definitely inferior results.

The following example is set forth to illustrate the process of the present invention.

EXAMPLE I

A nickel base alloy (Alloy 600) suspected of having plastic deformation was polished according to the procedure set forth in U.S. Pat. No. 4,304,779 cited above, to provide a substantially flow free surface on the alloy. The polished alloy was then electrolytically etched using a current density of less than 0.1 amp/cm$^2$. This condition was easily obtained by electrolytically etching approximately a 1 cm$^2$ surface area of the alloy with a 5% nital solution at 3 volts for about 20 seconds.

The etched surface was then subjected to a second electrolytic etch at a higher current density (e.g., 0.2 amp/cm$^2$). For this etching procedure, a 10% phosphoric acid etch for 3 to 6 seconds at 3 volts was sufficient.

The prepared article is now microscopically examined for alternating striations by using conventional interference contrast illumination. The article was detected to have these alternating striations confirming plastic deformation. Accordingly, the method of the present invention provides a simple, positive procedure for detecting plastic deformation in metal alloy articles.

While not being limited to a particular theory, applicants have postulated that the present invention is based upon the principle that the effects of plastic deformation remain within the microstructure of the metal alloy articles long after the metal articles have been stressed beyond their elastic limit. Accordingly, the development of the particular electrolytic etchant procedure of the present invention provides a simple and accurate procedure for testing metal alloy articles for plastic deformation.

The foregoing description of a preferred embodiment of the invention has been presented for purposes of illustration and description. It is not intended to be exhaustive or to limit the invention to the precise form disclosed, and obviously many modifications and variations are possible in light of the above teaching. The embodiment was chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

We claim:

1. A method of detecting low level plastic deformation in a metal alloy article consisting essentially of:
   (a) polishing the surface of said article to obtain a substantially flow free surface;
   (b) electrolytically etching said surface with nital at a current density of less than 0.1 amp/cm$^2$; and
   (c) microscopically examining said surface by interference contrast illumination to determine the presence of alternating striations, the presence of said striation indicating plastic deformation in said article.

2. The method of claim 1 wherein said etching step further comprises a second etch consisting essentially of electrolytically etching said surface with about 10% phosphoric acid at a current density greater than 0.1 amp/cm$^2$.

3. The method of claim 2 wherein said second etch is performed at a current density of about 0.2 amp/cm$^2$.

4. The method of claim 3 wherein the metal alloy article is selected from the group consisting of nickel base alloys and stainless steel.

5. The method of claim 2 wherein the metal alloy article is selected from the group consisting of nickel base alloys and stainless steel.

6. The method of claim 1 wherein the metal alloy article is selected from the group consisting of nickel base alloys and stainless steel.

* * * * *